United States Patent [19]
Clarke et al.

[11] Patent Number: 5,260,202
[45] Date of Patent: Nov. 9, 1993

[54] FERMENTATION METHOD

[75] Inventors: Peter M. Clarke; David J. Mead; Stephen H. Collins, all of Radcliffe on Trent, United Kingdom

[73] Assignee: Delta Biotechnology Limited, Nottingham, England

[21] Appl. No.: 41,666

[22] Filed: Apr. 1, 1993

Related U.S. Application Data

[63] Continuation-in-part of Ser. No. 469,505, Mar. 7, 1990.

[30] Foreign Application Priority Data

Sep. 7, 1988 [GB] United Kingdom ................ 8820951

[51] Int. Cl.$^5$ ...................... C12P 21/00; C12N 15/14
[52] U.S. Cl. .................. 435/71.1; 435/69.1; 435/69.6; 435/812
[58] Field of Search ................ 435/71.1, 69.1, 69.6, 435/812

[56] References Cited

U.S. PATENT DOCUMENTS

| | | | |
|---|---|---|---|
| 4,197,238 | 4/1980 | Murata et al. | 530/364 |
| 4,445,908 | 5/1984 | Compere et al. | |
| 4,914,027 | 4/1990 | Knapp et al. | 435/69.6 |
| 5,037,744 | 8/1991 | Knapp et al. | 435/69.6 |

FOREIGN PATENT DOCUMENTS

| | | |
|---|---|---|
| 0073646 | 3/1983 | European Pat. Off. |
| 0201239A1 | 11/1986 | European Pat. Off. |
| 0262516 | 4/1988 | European Pat. Off. |
| 0322984A1 | 6/1989 | European Pat. Off. |
| 8901046 | 9/1989 | PCT Int'l Appl. |
| 2127811A | 4/1984 | United Kingdom |

OTHER PUBLICATIONS

Hawkins et al. "The Human Serum Albumin Gene: Structure of a Unique Locus", Gene, 19 (1982) pp. 55-58.
Klebe et al., "A General Method for Polyethylene-Glycol-Induced Genetic Transformation of Bacteria and Yeast", 1983, Elsevier Science Publisher, Gene 25, pp. 333-341.
KI W K et al., "Development of Yeast Saccharomyces-Cere-Visiae Vector System for Eukaryotic Gene Cloning Optimum Condition for Intact Yeast Cell Transformation and Plasmid Stability in the Transformants", Korean J. Appln. Microbiol Bioeng 14(2), 1986, pp. 125-132.
Patent Cooperation Treaty, PCT/GB 89/01046, Sep. 6, 1989.

Primary Examiner—Herbert J. Lilling
Attorney, Agent, or Firm—R. Hain Swope; Larry R. Cassett

[57] ABSTRACT

The recoverable yield of recombinant human albumin in the fermentation of genetically engineered yeast that expresses the albumin and secretes it into the culture medium is increased by the addition of a stabilizing agent comprising a polyoxyalkylene compound, for example, polypropylene glycol or a polyoxypropylene/polyoxyethylene copolymer. The presence of these compounds in concentrations of from about 0.5 to 10 g per liter, preferably 1 to 5 g per liter, of fermentation broth prevents the degradation of the rHA produced under intensive fermentation conditions thereby raising the effective yield.

9 Claims, No Drawings

FERMENTATION METHOD

RELATED APPLICATIONS

This application is a continuation-in-part of U.S. Pat. application Ser. No. 07/469,505, filed Mar. 7, 1990.

This invention provides improved fermentation methods and, in particular, a method of increasing the quantity of recombinant human albumin (hereinafter "rHA") produced by fermentation of an rDNA-containing microorganism which is capable of secreting rHA into the culture medium.

BACKGROUND OF THE INVENTION

Human Serum Albumin ("HSA") is a major component of blood plasma and can be used as a plasma or serum substitute to treat burns, haemorrhagic shock and other conditions. Methods have been described whereby rHA can be produced by fermentation of microorganisms, i.e. suitable strains of bacteria and yeasts, into which the gene for HSA has been introduced by recombinant DNA technology (GB- A-2147903).

It is recognized by those skilled in the art that the expression vectors utilized to transform the microorganisms should be so constructed as to cause the microorganism to secrete rHA into the surrounding culture fluid. This is desirable because intracellular rHA, in common with many other heterologous proteins accumulated by microorganisms, is produced in an inactive, insoluble form from which the native protein can be obtained only with great difficulty (see, for example, M. Latta et al 1987 Bio Technology 5 1309-1314).

It is also recognized by those of ordinary skill in the art that, in order to maximize the productivity of the recombinant manufacturing process, it is desirable to grow the microorganisms in a highly agitated aerated fermenter thereby achieving high concentrations of cells and product. Unfortunately, these conditions leave the secreted protein exposed to physical, chemical and enzymatic degradation in the extracellular medium such that the quantity of recombinant protein recovered from the fermenter is much less than might have been expected from the performance of the microorganisms in less intensive conditions. This phenomenon is characteristic of the production of rHA.

Therefore, there exists a need to maximize the amount of rHA that is produced under such intensive conditions, particularly where such maximizing does not adversely affect the overall efficiency of the process. This need has been fulfilled in accordance with the present invention.

SUMMARY OF THE INVENTION

In accordance with the present invention, it has been found that the addition of certain chemical reagents to the fermentation media wherein rHA is produced and secreted by transformed microorganisms is effective in raising the concentration of recovered rHA, especially under intensive fermentation conditions and in minimal media, i.e. growth media which do not contain complex organic sources of nitrogen.

DETAILED DESCRIPTION OF THE INVENTION

The present invention is directed to an improvement in the production of recombinant human albumin ("rHA") in a transformed microorganism host wherein the rHA is produced by the microorganism and secreted into the surrounding medium. The production and secretion of rHA by microorganisms, such as certain bacteria and yeasts, transformed by recombinant techniques is known. The genetic materials and techniques necessary to effect the transformation of the microorganisms are likewise known.

The concentration of recoverable rHA produced in minimal media in accordance with the present invention is substantially enhanced by the addition thereto of a stabilizing agent comprising one or more polyoxyalkylene polymers. Any suitable polyoxyalkylene polymer or copolymer with another compound may be used, for example polyethylene glycol; polypropylene glycol; polysorbate 80; copolymers of ethylene oxide and propylene oxide; and copolymers of ethylene oxide and/or propylene oxide with other compounds, such as fatty acids, fatty alcohols, sugars and polyols, for example sugar alcohols (e.g. sorbitol), ethylene glycol, pentaerythritol and glycerol.

Polyoxypropylene polymers have the general formula $HO\text{-}(CH_2\text{---}CH(CH_3)\text{---}0)_n\text{---}H$. Suitable polyoxyethylene-polyoxypropylene copolymers include those which can be represented as $X\text{---}[(0\text{---}CH_2\text{---}CH(CH_3)\text{---}0)_m\text{---}(CH_2\text{---}CH_2O)_n\text{---}H]_L$ where X is a fatty acid, fatty alcohol, sugar or polyol, L is 1-6, m is 10-30 and n is 0-10. Another suitable series of compounds uses as the polyol polyethylene glycol which has two available hydroxyl groups, each substitutable by an $\text{---}0(CH_2\text{---}CH(CH_3)\text{---}0)_n\text{---}H$ group where each n may independently be 0-10. Effective reagents include polypropylene glycol (average molecule weight 2,000) and "polyricinate", a condensate of castor oil fatty acids and ethylene oxide produced by Croda Surfactants Ltd. Preferred compounds include those available under the trade designations "Darastil", for example, "Darastil 8231") (Grace Dearborn Ltd) and Breox FMT30 (BP Chemicals Ltd).

All of the compounds and classes of compounds described above are referred to herein as "polyoxyalkylene compounds". These compounds are usually, but not always, antifoam compounds. The use of such compounds as foam suppressants in fermentation media such as contemplated herein is known. However, the levels of polyoxyalkylene compounds utilized in accordance with the present invention are substantially in excess of even the maximum levels conventionally utilized for foam control.

High cell densities in microbial fermentations are commonly achieved by fed-batch culture. Under such conditions, the fermenter is typically only partially full at the start of the process and contains only a small fraction of the carbon substrate. As fermentation proceeds, a concentrated solution of the carbon substrate, and possibly other nutrients, is gradually added. Foam control in such a process in commonly achieved by a sensor situated near the top of the fermenter which automatically actuates the addition of an antifoam agent when foam is detected. Although antifoam agents are a common process aid in such a process, because the fermenter is only partially filled at the start, antifoam agents are typically added only toward the end of the process when, as the vessel fills, a head of foam will reach and actuate the sensor.

Typical total usage rates for an antifoam agent in such a sensor-controlled process are 0.02-0.2 g per liter of fermentation broth. In contrast, in the process improvement of the present invention, the beneficial effect of the stabilizing agent is realized throughout the process and, therefore, it is added to the initial fermentation medium or at an early stage of the fermentation process. Those of ordinary skill in the art will appreciate that the subject stabilizing agents are beneficial throughout the fermentation process. Therefore, while it is not intended that the subject invention be limited to a particular early stage of the fermentation process, initial or early addition is of maximum benefit. The stabilizing agent may be added either in a single large dose at or near the start of fermentation, or by an initial dose followed by gradual or intermittent additions throughout the process. In this way it is possible to maintain or increase the concentration of the stabilizing agent during the fermentation process.

One or more suitable stabilizer compounds may be used. Usage rates for this process are such as to yield a concentration of stabilizer agent, or of total stabilizer agents if more than one is used, of between about 0.5 and 10 g, preferably between about 1 and 5 g, per liter of fermentation media. In a preferred embodiment of the subject invention, the concentrations of polyoxyalkylene stabilizing agent(s) in the initial fermentation broth is about 1 g per liter, which concentration is maintained or increased by suitable additions throughout the fermentation process. Although the use of fed-batch culture is particularly suitable for the production of high cell densities for heterologous protein production, the process is not restricted to this type of fermentation. Use of these reagents at these concentrations is also applicable to the production of rHA in simple batch culture or in continuous culture. In the latter case, the stabilizer agent can be added continuously or intermittently to maintain a concentration in the desired range of 0.5-10 g, preferably 1-5 g, per liter of fermentation media.

The use of the stabilizer agents of the invention has been found to be beneficial with relatively low-yielding strains of yeast. With certain strains of yeast, which give higher yields of rHA, the beneficial effect is still detectable, but may be less noticeable if the fermentation protocol is such as to produce high cell densities.

The rHA may be any naturally-occurring or modified form of albumin, including fragments thereof, provided that the compound retains at least one functional characteristic of HSA, for example its oncotic or ligand-binding properties or its utility in laboratory media. In particular, the rHA may be the fragment disclosed in EP-A-322 094. Secretion may be mediated by any suitable signal sequence, for example the pre-HSA sequence or the yeast alpha-factor signal sequence.

The microorganism may be any organism (including animal or plant cell cultures) which secretes albumin into the fermentation medium, such as suitable strains of bacteria (for example Bacillus or Streptomyces spp.) or yeasts (such as *Saccharomyces cerevisiae* or *Kluyveromyces lactis*). Transformation of the microorganism so that it will express and secrete rHA may be carried out by any art-recognized technique such as described above. The nutrient media may be any conventional media or modification thereof to be adopted to the growth of the microorganism being utilized. Formulation of a suitable culture medium to optimize conditions for a given microorganism is considered to be with the skill of the art.

The following Examples further illustrate the invention, it being understood that the invention is not intended to be limited to the details disclosed therein.

EXAMPLE 1

Stabilization of Albumin in Fermentation Medium

A laboratory fermenter equipped with a conventional foam sensor was filled to half its nominal working volume with an initial "batch" medium containing 50 ml per liter of a salts mixture consisting of, on a per liter basis: 114 g $KH_2PO_4$; 12 g $MgSO_4$; 3.0 g $CaCl_2.6H_2O$; and 2.0 g $Na_2$ EDTA, 10 ml per liter of a trace elements solution containing, on a per liter basis, 3 g $ZNSO_4.7H_2O$; 10 g $FESO_4.7H_2O$; 3.2 g $MnSO_4.4H_2O$; 0.79 g $CUSO_4.5H_2O$; 1.5 g $H_3BO_3$; 0.2 g KI; 0.5 g $Na_2MoO_4.2H_2O$; and 0.56 g $CoCl_2.6H_2O$, 50 ml per liter of a vitamins mixture containing, on a per liter basis: 1.6 g Ca pantothenate; 1.2 g nicotinic acid; 12.8 gl m inositol; 0.32 g thiamine HCl; 0.8 g pyridoxine HCl ; and 8 mg biotin, 75 ml $H_3PO_4$, and 20 g sucrose. An equal volume of "feed" medium containing in each liter 100 ml of the salts mixture, 20 ml of the trace elements solution, 500 g of sucrose and 100ml of the vitamin solution was held in a separate reservoir connected to the fermenter by a metering pump.

Albumin, 500 mg per liter, was added to the fermenter which was then inoculated with *Saccharomyces cerevisiae* transformed with a plasmid which codes for the production and secretion of albumin. The pH was maintained at 5.7% 0.2 by automatic addition of ammonia or sulfuric acid, the temperature was kept at 30° C. and the stirrer speed was adjusted to give a dissolved oxygen tension (DOT) of >20% air saturation at 1 v/v/min air flow rate. When the initial substrate had been consumed, the metering pump was turned on, maintaining a growth rate of approximately 0.15 $h^{-1}$. The pump rate was increased to maintain this growth rate until the stirrer speed reached its maximum value at which point it was not possible to increase the pump rate any further without causing the DOT to fall below 15% air saturation which was the minimum value permitted to occur. Polypropylene glycol 2000 was automatically added by the foam sensor when the level of foam became sufficiently high to activate addition. This did not occur until over 50% of the feed solution had been added. The final level of addition was 0.2 g/l. The biomass concentration at the end of the fermentation was 93 g/l. About 90% of the albumin initially present was degraded within 24 h of the start of the feed.

In a subsequent experiment under otherwise identical conditions, one gram per liter of polypropylene glycol was added at the start of fermentation. The progress of the fermentation was very similar, reaching a final dry weight of 94 g/l. However, the level of albumin degradation was significantly reduced so that, at the conclusion of the fermentation, only about 40% of the albumin originally present was degraded.

EXAMPLE 2

The procedure of Example 1 was repeated in a series of fermentation runs with the modification that the pump rate was increased automatically using a computer control system which monitored respiratory quotient (RQ) so that the feed rate was reduced if RQ exceeded 1.2. Those of ordinary skill in the art will appreciate that this procedure avoids possible yield loss by the "Crabtree" effect. In all cases fermenters were inoculated with *Saccharomyces cerevisiae* transformed with a plasmid which codes for secreted albumin production.

The following protocols were used for the addition of a polyoxyalkylene compound with the following results.

Fermentation A

Comparative Example

Polypropylene glycol 2000 added solely in response to the foam sensor. Addition began after the initiation of fermentation, increasing to 0.1 g per liter after 10% of the feed had been added, and rising to a final level of 0.2 g per liter during the last 50% of the feed. The final biomass was 84 g/l, and the albumin level was determined on an arbitrary scale to be 1.0 unit.

Fermentation B

The initial medium contained 1.5 g per liter of polyricinate. The concentration was increased to 2.2 g per liter after 35% of feed had been added with further increases to maintain a level of 2.5 g/l when feed was nearly complete. A further addition after the feed was completed raised the final level to 3.5 g per liter. The final biomass was 83 g per liter and the albumin level was 3.81 units.

Fermentation C

The initial medium contained 1.5 g per liter of polypropylene glycol. Additions were made after 50% and 80%, respectively, of the feed had been added to maintain this concentration. The final biomass was 86 g per liter and the albumin concentration was 4.2 units.

EXAMPLE 3

A series of the fed-batch fermentations were carried out according to the procedure of Example 2-C except that a different strain of transformed *S. cerevisiae* was used. A different compound, commercially available as an antifoam, was added to each fermentation. The results are reported in the following table.

| Antifoam Preparation | Biomass (g/l) | Albumin Concentration (arbitrary units) |
|---|---|---|
| Arachis oil | 95.4 | 1.0 |
| Crill 1 | 86.8 | 0.8 |
| Breox FMT30 | 81.8 | 3.2 |
| Darastil 8231 | 81.6 | 2.5 |

The four preparation utilized in this example are further defined as follows: Arachis Oil (Peanut oil); Crill 1 (Sorbital monolaurate available from Croda Surfactants Ltd.); Breox FMT 30 (Block copolymer of polyethylene glycol and polypropylene glycol having a molecular weight of approximately 3,000, available from BP Chemicals Ltd.); and Darastil 8231 (Block copolymer of polyethylene glycol and polypropylene glycol having a molecular weight of approximately 2,000, available from Grace Dearborn Ltd.). It is readily apparent that the preparations that are polyoxyalkylene compounds gave markedly superior results than the others in terms of higher albumin yields.

I claim:

1. In a process of recovering recombinant human albumin from a fermentation medium wherein an albumin-secreting microorganism is fermented in a suitable medium under conditions such that the microorganism produces said albumin and secretes it into the medium from which it is recovered, the improvement wherein a stabilizing agent consisting of one or more polyoxyalkylene polymers is added to the medium at or near the beginning of fermentation to from about 0.5 to about 10 g per liter of said medium.

2. A process in accordance with claim 1, wherein the polyoxyalkylene stabilizing agent added to from about 1.0 to about 5.0 g per liter of medium.

3. A process in accordance with any claim 1, wherein the polyoxyalkylene stabalizing agent is selected from the group consisting of polypropylene glycol, a condensate of castor oil fatty acids and ethylene oxide, a copolymer of propylene oxide and ethylene oxide with a polyol and a copolymer of propylene oxide and polyethylene glycol.

4. A process in accordance with claim 1, wherein the microorganism is a yeast.

5. A process in accordance with claim 4, wherein the yeast is *Saccharomyces cerevisiae*.

6. A process in accordance with claim 1, wherein the medium is a minimal medium.

7. A process in accordance with claim 1, wherein additions of said stabilizing agent are made either continuously or intermittently during fermentation to maintain the approximate concentration of the stabilizing agent initially added to the medium.

8. A process in accordance with claim 7, wherein said stabilizing agent is present in at least about 1 g per liter throughout said fermentation.

9. A process in accordance with claim 1, wherein additions of said stabilizing agent are made either continuously or intermittently during fermentation to increase the concentration of stabilizing agent throughout the fermentation to a final concentration not in excess of about 10 g/l.

* * * * *